(12) United States Patent
Rapoport et al.

(10) Patent No.: US 11,052,016 B2
(45) Date of Patent: Jul. 6, 2021

(54) DEVICES, SYSTEMS AND METHODS FOR REDUCING MOTION ARTIFACTS DURING IMAGING OF A NEONATE

(71) Applicant: Aspect Imaging Ltd., Shoham (IL)

(72) Inventors: Uri Rapoport, Moshav Ben Shemen (IL); Shmuel Azulay, Tel Aviv (IL)

(73) Assignee: Aspect Imaging Ltd., Shoham (IL)

(*) Notice: Subject to any disclaimer, the term of this patent is extended or adjusted under 35 U.S.C. 154(b) by 70 days.

(21) Appl. No.: 16/251,506

(22) Filed: Jan. 18, 2019

(65) Prior Publication Data

US 2019/0216676 A1    Jul. 18, 2019

Related U.S. Application Data

(60) Provisional application No. 62/618,653, filed on Jan. 18, 2018.

(51) Int. Cl.
| | | |
|---|---|---|
| *A61G 11/00* | (2006.01) | |
| *A61H 11/00* | (2006.01) | |
| *A61B 6/04* | (2006.01) | |
| *G01R 33/565* | (2006.01) | |
| *G01R 33/563* | (2006.01) | |

(Continued)

(52) U.S. Cl.
CPC ............ *A61H 11/00* (2013.01); *A47C 21/006* (2013.01); *A47L 9/02* (2013.01); *A61B 6/04* (2013.01); *A61G 11/00* (2013.01); *G01R 33/56308* (2013.01); *G01R 33/56509* (2013.01); *A61B 6/0407* (2013.01)

(58) Field of Classification Search
CPC .............................. A61G 11/00; A61G 11/008
USPC ....................................................... 600/21–22
See application file for complete search history.

(56) References Cited

U.S. PATENT DOCUMENTS

| 1,900,342 A | 3/1933 | Hess |
|---|---|---|
| 2,638,087 A | 5/1953 | Livsey |

(Continued)

FOREIGN PATENT DOCUMENTS

| CA | 2815746 | 5/2012 |
|---|---|---|
| CN | 2448344 | 9/2001 |

(Continued)

OTHER PUBLICATIONS

Antonucci, et al., The infant incubator in the neonatal intensive care unit: unresolved issues and future developments, J. Perinat. Med. 37(2009), 587-598.

(Continued)

*Primary Examiner* — John P Lacyk
(74) *Attorney, Agent, or Firm* — Loeb & Loeb, LLP

(57) ABSTRACT

Generally, a system for soothing a baby during imaging by an imaging device is provided. The system can include: a capsule incubator for positioning the baby within the imaging device, the capsule incubator can include: a bottom portion having an inner surface, a bed positioned on top of the inner surface for positioning the baby thereon, and one or more members coupled to the bottom portion that are positioned in a first position to open the capsule incubator and a second position to close the capsule incubator; a vibrational device including a vibrational element that extends from outside of the capsule incubator into the capsule incubator and is coupled to the bed to cause the bed to vibrate with a predetermined vibrational frequency, thus causing the baby to vibrate with the predetermined vibrational frequency.

16 Claims, 11 Drawing Sheets

(51) Int. Cl.
*A47C 21/00* (2006.01)
*A47L 9/02* (2006.01)

(56) References Cited

U.S. PATENT DOCUMENTS

| | | | |
|---|---|---|---|
| 2,708,927 A | 5/1955 | Dixon et al. |
| 3,012,836 A | 12/1961 | Smith et al. |
| 3,315,671 A | 4/1967 | Creelman |
| 3,470,866 A | 10/1969 | Gittelson |
| 3,655,178 A | 4/1972 | Vezina |
| 3,710,791 A | 1/1973 | Deaton |
| 3,920,000 A | 11/1975 | Atherton et al. |
| 4,161,172 A | 7/1979 | Pickering |
| 4,509,505 A | 4/1985 | Mercey et al. |
| 4,567,894 A | 2/1986 | Bergman |
| 4,712,263 A | 12/1987 | Pronzinski |
| 4,750,474 A | 6/1988 | Dukhan et al. |
| 4,936,824 A | 6/1990 | Koch et al. |
| 5,028,872 A | 7/1991 | Nakabayashi |
| 5,059,906 A | 10/1991 | Yamanaka |
| 5,100,375 A | 3/1992 | Koch |
| 5,446,934 A | 9/1995 | Frazier |
| 5,509,159 A | 4/1996 | Du-Bois |
| 5,534,669 A | 7/1996 | Schroeder et al. |
| 5,759,149 A | 6/1998 | Goldberg et al. |
| 5,797,833 A | 8/1998 | Kobayashi et al. |
| 5,800,335 A | 9/1998 | Koch et al. |
| 5,817,003 A | 10/1998 | Moll et al. |
| 5,917,324 A | 6/1999 | Leussler |
| 5,943,716 A | 8/1999 | Chu |
| 5,971,913 A | 10/1999 | Newkirk et al. |
| 6,036,634 A | 3/2000 | Goldberg et al. |
| 6,142,963 A | 11/2000 | Black et al. |
| 6,155,970 A | 12/2000 | Dykes et al. |
| 6,193,285 B1 | 2/2001 | Proctor |
| 6,231,499 B1 | 5/2001 | Jones |
| D446,675 S | 8/2001 | Straub |
| 6,317,618 B1 | 11/2001 | Livni et al. |
| 6,409,654 B1 | 6/2002 | McClain et al. |
| 6,433,548 B1 | 8/2002 | Furuta et al. |
| 6,471,634 B1 | 10/2002 | Dykes et al. |
| 6,511,414 B1 | 1/2003 | Hamsund |
| 6,611,702 B2 | 8/2003 | Rohling et al. |
| 6,641,521 B2 | 11/2003 | Kolarovic |
| 6,666,816 B2 | 12/2003 | Mountain |
| RE38,453 E | 3/2004 | Lessard et al. |
| 6,776,527 B1 | 8/2004 | Tybinkowski et al. |
| 6,860,272 B2 | 3/2005 | Carter et al. |
| 6,992,486 B2 | 1/2006 | Srinivasan |
| 7,255,671 B2 | 8/2007 | Boone et al. |
| 7,278,962 B2 | 10/2007 | Lonneker-Lammers |
| D567,948 S | 4/2008 | Tierney et al. |
| 7,482,558 B2 | 1/2009 | Koch |
| 7,599,728 B2 | 10/2009 | Feenan |
| 7,784,121 B2 | 8/2010 | Ahlman |
| 8,034,007 B2 | 10/2011 | Avitable |
| 8,127,384 B2 | 3/2012 | Carlton |
| 8,147,396 B2 | 4/2012 | Srinivasan |
| 9,974,705 B2 | 3/2018 | Rapoport |
| 2001/0049465 A1 | 12/2001 | Goldberg et al. |
| 2002/0072648 A1 | 6/2002 | Dykes et al. |
| 2002/0123681 A1 | 9/2002 | Zuk et al. |
| 2002/0143233 A1 | 10/2002 | Donnelly et al. |
| 2002/0173696 A1 | 11/2002 | Kolarovic et al. |
| 2002/0173717 A1 | 11/2002 | Rohling et al. |
| 2003/0088175 A1 | 5/2003 | Branch et al. |
| 2004/0030241 A1 | 2/2004 | Green et al. |
| 2004/0034273 A1 | 2/2004 | Boris |
| 2004/0133064 A1 | 7/2004 | Castillon Levano et al. |
| 2004/0186341 A1 | 9/2004 | McDermott |
| 2004/0236174 A1 | 11/2004 | Boone et al. |
| 2004/0236175 A1 | 11/2004 | Boone et al. |
| 2005/0004422 A1 | 1/2005 | Caspary et al. |
| 2005/0020906 A1 | 1/2005 | Seijger et al. |
| 2005/0038314 A1 | 2/2005 | Falk |
| 2005/0113668 A1 | 5/2005 | Srinivasan |
| 2006/0079730 A1 | 4/2006 | Getsla |
| 2007/0232894 A1 | 10/2007 | Feenan |
| 2008/0163425 A1 | 7/2008 | White |
| 2009/0044335 A1 | 2/2009 | Brewin et al. |
| 2009/0209846 A1 | 8/2009 | Bammer |
| 2010/0004502 A1 | 1/2010 | Honma et al. |
| 2010/0010599 A1 | 1/2010 | Chen et al. |
| 2010/0168502 A1 | 7/2010 | Delaporte et al. |
| 2010/0231014 A1 | 9/2010 | Gibree et al. |
| 2010/0262050 A1 | 10/2010 | Gasparovich |
| 2010/0315085 A1 | 12/2010 | Brown |
| 2011/0048424 A1 | 3/2011 | Radko |
| 2011/0113555 A1 | 5/2011 | Smith |
| 2011/0125010 A1 | 5/2011 | Vaquero Lopez et al. |
| 2011/0160521 A1 | 6/2011 | Khodak et al. |
| 2012/0078034 A1 | 3/2012 | Falk et al. |
| 2012/0126814 A1 | 5/2012 | Fischer et al. |
| 2012/0140899 A1 | 6/2012 | Bailey et al. |
| 2012/0247488 A1 | 10/2012 | Tonks |
| 2013/0025062 A1 | 1/2013 | Esch |
| 2013/0109956 A1 | 5/2013 | Rapoport |
| 2013/0150656 A1 | 6/2013 | Falk et al. |
| 2013/0204074 A1 | 8/2013 | Belval et al. |
| 2013/0204617 A1 | 8/2013 | Kuo et al. |
| 2013/0267765 A1 | 10/2013 | Rapoport |
| 2013/0334439 A1 | 12/2013 | Etters |
| 2014/0003614 A1 | 1/2014 | Levitov et al. |
| 2014/0051976 A1 | 2/2014 | Rapoport et al. |
| 2014/0078301 A1 | 3/2014 | Fazzi et al. |
| 2014/0098934 A1 | 4/2014 | Kondo |
| 2014/0099010 A1 | 4/2014 | Rapoport |
| 2014/0117989 A1 | 5/2014 | Rapoport |
| 2014/0354279 A1 | 12/2014 | Dumoulin et al. |
| 2014/0357981 A1 | 12/2014 | Dumoulin |
| 2014/0364722 A1 | 12/2014 | Dumoulin |
| 2015/0020308 A1 | 1/2015 | Reichle |
| 2015/0137812 A1 | 5/2015 | Rapoport |
| 2015/0141799 A1 | 5/2015 | Rapoport et al. |
| 2016/0030264 A1 | 2/2016 | Lehmann et al. |
| 2016/0081582 A1 | 3/2016 | Rapoport |

FOREIGN PATENT DOCUMENTS

| | | |
|---|---|---|
| CN | 102551719 | 7/2012 |
| DE | 19617739 | 6/1997 |
| EP | 1132072 | 9/2001 |
| EP | 2581071 | 4/2013 |
| JP | 2004531313 | 10/2004 |
| JP | 2005514078 | 5/2005 |
| JP | 2007252741 | 10/2007 |
| JP | 2010178857 | 8/2010 |
| JP | 2016539683 | 12/2016 |
| WO | WO1998048756 | 11/1998 |
| WO | WO9921526 | 5/1999 |
| WO | WO2008137003 | 11/2008 |
| WO | WO2010054457 | 5/2010 |
| WO | WO2011109761 | 9/2011 |
| WO | WO2012143825 | 10/2012 |
| WO | WO2013115847 | 8/2013 |

OTHER PUBLICATIONS

Baby Pod II Infant Transport Device, Advance Healthcare Technology, 2011, brochure, pp. 1-6.
Baby Pod II Operation and Maintenance Manual, revision 5, Jan. 2011, pp. 1-11.
Ferris et al., The design of neonatal incubators: a systems-oriented, human centered approach, J. Perinatology, 2013, 33, S24-S31.
Kim et al., Air transparent soundproof window, AIP Advances 4, 117123 (2014), published online, doi: http://dx.doi.org/10.1063/1.4902155.
Knutson, Allysa Jennie, Acceptable noise levels for neonates in the neonatal intensive care unit, A Capstone Project submitted in partial fulfillment of the requirements for the degree of: Doctor of Audiology, Washington University School of Medicine Program in Audiology and Communication Sciences, May 17, 2013, pp. 1-59.

(56) References Cited

OTHER PUBLICATIONS

Liu, Lichuan et al., Development and Applications of Active Noise Control System for Infant Incubators, Proceedings of the 2009 IEEE International Conference on Systems, Man, and Cybernetics San Antonio, TX, USA—Oct. 2009, pp. 1-6.
Mahil et al., Hybrid Swarm Algorithm for the Suppression of Incubator Interference in Premature Infants ECG, Research Journal of Applied Sciences, Engineering and Technology 6(16): 2931-2935, 2013.
Marik et al., Neonatal incubators: A toxic sound environment for the preterm infant?, Pediatr Crit Care Med 2012 vol. 13, No. 6, pp. 1-6.
Paley et al., An MR-compatible neonatal incubator, The British Journal of Radiology, 85, 2012, 952-958.
American National Standard, Medical Electrical Equipment—Parts 2-19: Particular requirements for the basic safety and essential performance of infant incubators, Association for the advancement of medical instrumentation, ANSI/AAI/IEC 60601-2-19:2009, pp. 1-19.
Ranganna et al., Reducing noise on the neonatal unit, Infant, 2011, vol. 7, Issue 1, pp. 25-28.
Jenkins, S., ScanPod, BabyPod-Products-ScanPod, 2002-2011 Advance Healthcare Technology, ltd., internet website http://babypod.com:80/products/scanpod.php.
Science Daily, Inside the preemie brain, Incubator enables MRI scans on premeeies for preventing birth asphyxia, Dec. 1, 2005, pp. 1-2, Web address: http://web.archive.org/web/20130303154220/http://www.sciencedaily.com/videos/2005/1211-inside_the_preemie_brain.htm.
Kitterman et al., Catheterization of umbilical vessels in newborn infants, Pediatric Clinics of North America, vol. 17, No. 4, Nov. 1970, 895-912.
Thermaxx Jackets, 5 most common thermal insulation materials, pp. 1-4, internet: https://www.thermaxxjackets.com/5-most-common-thermal-insulation-materials/.

US 11,052,016 B2

DEVICES, SYSTEMS AND METHODS FOR REDUCING MOTION ARTIFACTS DURING IMAGING OF A NEONATE

CROSS REFERENCE TO RELATED APPLICATIONS

This application claims priority to U.S. Provisional Application No. 62/618,653 filed on Jan. 18, 2018, which is incorporated herein by reference in its entirety.

FIELD OF THE INVENTION

The present invention relates to the field of imaging a baby, and more particularly, to a system and method for minimizing movements, thus reducing motion artifacts, of a baby positioned within a neonate incubator during imaging where the baby is soothed via a vibration.

BACKGROUND OF THE INVENTION

Neonates (e.g., human babies) are typically kept within an incubator when receiving medical treatment in a hospital. The incubator can provide constant environmental conditions (e.g., temperature, humidity, noise level, vibration level, light level, and/or bacteria/germ) appropriate for life support of a baby and to support recovery of the baby. Baby incubators typically also allow for connection of various life support equipment and/or monitors to the baby and the incubator to, for example, provide feeding, monitor feeding, perform fluid exchange and/or monitor/control cardiac activity.

During medical treatment of a baby, procedures and/or imaging of the baby can require moving the baby out of the incubator about the hospital. Transporting the baby can require moving the baby from its controlled environment within the incubator, and in some instances, can require detaching/reattaching life support equipment attached to the baby (e.g., mechanical ventilation, oxygen, intravenous medications/hydration, etc.).

Transporting the baby can also require that the baby be picked up and repositioned into a transport device (e.g., a large transport incubator), which can disturb physical position and/or environment of the baby. For example, for a baby that has had surgery, it can be important to move the baby as minimally as possibly, to reduce risk of opening stitches and/or allowing infection to enter wound sites.

Transporting the baby can also require that every surface the baby touches and piece of connected/disconnected equipment be sterilized to, for example, prevent unwanted germs (e.g., staph infections) from infecting the baby.

Transporting the baby is typically done in a large incubator. This can be heavy and, in some instances, require multiple medical personnel to transport the baby.

When a baby on life support is transported, it can require such a disruption to the baby, that many times, the detriment of the disruption to the baby can outweigh the benefits that can be obtained from the reason for the transport (e.g., medical imaging of the baby's anatomy).

Therefore, it can be desirable to transport a baby for medical procedures without having to remove the baby from its controlled environment and/or detach/reattach life support equipment.

Some types of medical procedures (e.g., magnetic resonance imaging) can require magnetic and/or radio frequency (RF) shielding of life support equipment, elimination of magnetic materials in the vicinity of the baby being imagined, and/or addition of elements (e.g., an RF coil) into the environment of the baby, thus creating further disturbance to the environment of the baby.

Performing imaging of a baby can be an important diagnostic tool for a doctor. Imaging devices can be used to obtain images of a human's anatomy. For example, magnetic resonance imaging (MRI) devices can be used to create three-dimensional sections and/or layered images of body organs and/or tissue.

Other types of imaging devices that can require transporting a baby include x-ray radiography, ultrasound, elastography, tactile imaging, thermography, positron emission tomography (PET) and/or single-photon emission computer tomography (SPECT).

For some imaging devices, it can be important for the patient to remain as motionless as possible as motion can distort the image. For example, MRI devices typically use a powerful magnet to create a magnetic field. The magnetic field can cause the nuclei atoms within a body to align with the magnetic field. Radio waves are typically applied to the body to cause the nuclei to change their alignment. When the radio waves are removed, the nuclei can relax back into their previous state. As the nuclei return to their previous state, they can emit distinct radio signals. The rate at which the nuclei emit signals and the frequency of the signals can depend on a type of the atom. Motion of the patient during imaging can cause distortion of the signals.

MRI devices can use a first radio frequency (RF) coil to generate the radio waves, which can be sometimes referred to as a gradient field, and a second RF coil to receive the radio waves or can use the same RF coil to both transmit and/or receive.

MRI devices for medical diagnoses typically include a bore that a patient lying on a bed gets inserted into for imaging. The MRI devices are typically deployed in an MRI safe room in a hospital. The MRI safe room typically requires that all magnetic materials be left outside of the MRI room, so that they don't get pulled towards the MRI device by the force of the magnetic field to, for example, cause accidents. The MRI safe room also typically includes a RF shield in its walls. The RF shield can ensure that RF interference from outside of the MRI room does not compromise the MRI images, and can also ensure that RF energy generated by the MRI does not exit the room.

MRI imaging a patient connected to life support typically requires the patient be completely disconnected from all life support equipment, and reconnected to the life support equipment via very long tubing that is threaded through a hole in the MRI room, such that, for example, the life support equipment is outside of the MRI room and away from interference that can be caused by RF waves and/or magnetic energy. Additionally, MRI rooms are typically kept at a cold temperature, so that the magnets of the MRI don't overheat.

Obtaining MRI images of babies can require that the baby be moved out of its incubator into an uncontrolled environment (e.g., a cold/loud MRI room), all of the life support equipment be disconnected and reconnected (e.g., to move the baby into a transport incubator and/or to change/thread tubes of the life support equipment through a hole in the MRI room), placement of the baby on the same MRI bed that a non-baby patient is placed on and/or extensive and/or repeated sterilization of the MRI bed and/or life support equipment.

Therefore, it can be desirable to obtain an MRI image of a baby, where the baby is as motionless as possible, where the baby does not need to be moved from an incubator into an MRI and/or where equipment that soothes and supports the baby does not is substantially RF shielded and does not substantially interfere with quality of the MRI image.

SUMMARY OF THE INVENTION

In one aspect, the invention includes a system for soothing a baby during imaging by an imaging device. The system includes a capsule incubator for positioning the baby within the imaging device. The capsule incubator includes a bottom portion having an inner surface, a bed positioned on top of the inner surface for positioning the baby thereon, and one or more members coupled to the bottom portion that are positioned in a first position to open the capsule incubator and a second position to close the capsule incubator. The system also includes a vibrational device, the vibrational device including a vibrational element that extends from outside of the capsule incubator into the capsule incubator and is coupled to the bed to cause the bed to vibrate with a predetermined vibrational frequency, thus causing the baby to vibrate with the predetermined vibrational frequency.

In some embodiments, the system is operable with a magnetic resonance imaging (MRI) device and the capsule incubator includes a radio frequency (RF) shield that detachably mates with a first incubator end of the capsule incubator, the RF shield comprising a conduit having a first aperture and a second aperture, and wherein the vibrational element extends from the outside of the capsule incubator into the capsule incubator through the conduit.

In some embodiments, the conduit has a length to width ratio of at least 5 to 1. In some embodiments, the vibrational device further includes a vibrations generator positioned outside of the capsule incubator, and wherein the vibrational element is a rod coupled to the vibrations generator. In some embodiments, the vibrational device further includes a fluid pump positioned outside of the capsule incubator, and the vibrational element is a fluid conduit coupled to the fluid pump.

In some embodiments, the system includes a cart detachably connectable to the first incubator end of the capsule incubator and capable of transporting the capsule incubator and of positioning the capsule incubator within the imaging device. In some embodiments, the system includes a controller in communication with the vibrational device and the imaging device, the controller to at least one of stop the vibrations generated by the vibrational device each time the imaging device scans and synchronize the imaging device to perform scans at the same relative location in the vibration cycle of vibrational device.

In another aspect, the invention includes a system for housing, transporting and imaging a baby. The system includes a magnetic resonance imaging (MRI) device including a magnetic field assembly comprising at least one magnet, at least one radiofrequency (RF) coil and a bore, the magnetic field assembly to generate a magnetic field to carry out the imaging of the baby, and a housing to at least partly surround the magnetic field assembly and to substantially eliminate a magnetic fringe field generated by the magnetic field assembly outside of the housing. The system also includes a capsule incubator for positioning the baby within the bore of the MRI device, the capsule incubator including a bottom portion having an inner surface, a bed positioned on top of the inner surface for positioning the baby thereon, one or more members coupled to the bottom portion that are positioned in a first position to open the capsule incubator and a second position to close the capsule incubator, and a radio frequency (RF) shield that detachably mates with a first incubator end of the capsule incubator and closes the bore of the MRI device when the capsule incubator is positioned therein, the RF shield comprising a conduit having a first aperture and a second aperture. The system also including a vibrational device including a vibrations generator positioned outside the capsule incubator and capable of generating vibrations at a predetermined vibrational frequency, and a non-magnetic vibrational element that extends from outside of the capsule incubator into the capsule incubator through the conduit and is coupled to the vibrations generator at a first element end and to the bed at a second element end to cause the bed to vibrate with the predetermined vibrational frequency, thus causing the baby to vibrate with the predetermined vibrational frequency, wherein the predetermined frequency is based on a frequency that a particular baby finds soothing and likely to cause the particular baby to sleep.

In some embodiments, the conduit has a length to width ratio of at least 5 to 1. In some embodiments, the vibrations generator is a rotational or an electrical device. In some embodiments, the vibrations generator is a fluid pump and the vibrational element is a non-magnetic fluid conduit. In some embodiments, the system further includes a cart detachably connectable to the first incubator end of the capsule incubator and capable of transporting the capsule incubator and of positioning the capsule incubator within the imaging device.

In some embodiments, the system includes a controller in communication with the vibrational device and the MRI device, the controller to at least one of stop the vibrations generated by vibrational device each time the MRI device scans and synchronize the MRI device to perform scans at the same relative location in the vibration cycle of vibrational device.

In one aspect, the invention involves a method of soothing a baby during imaging by an imaging device. The method involves determining a vibrational frequency at which the baby is soothed, vibrating, by a vibrational device, a bed movably positioned within a capsule incubator located in the imaging device at the predetermined vibrational frequency, thereby soothing the baby resting on the bed, and obtaining, by the imaging device, at least one image of at least a portion of the baby.

In some embodiments, the method involves providing a radiofrequency (RF) and/or magnetic shield to the vibrational device to prevent from RF and/or magnetic radiation generated by the MRI device to interfere with the vibrational device.

In some embodiments, the method involves stopping the vibrations generated by the vibrational device each time the imaging device scans, synchronizing the imaging device to perform scans at the same relative location in a vibrational cycle of the vibrational device, and filtering the at least one image to correct for a phase effect generated by scanning different spatial locations at different times during the vibrational cycle of the vibrational device.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings.

Figure 1A:
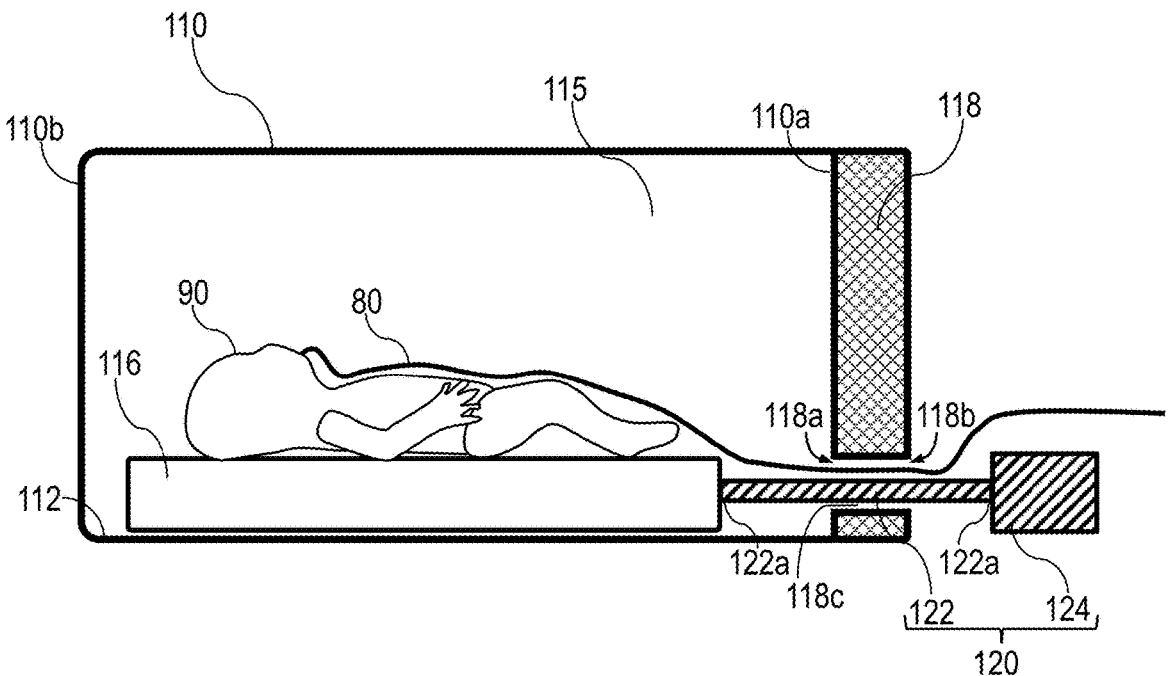
FIGS. 1A and 1B are schematic illustrations of a system for soothing a baby during imaging, according to some embodiments of the invention.

It will be appreciated that, for simplicity and clarity of illustration, elements shown in the figures have not necessarily been drawn to scale. For example, the dimensions of some of the elements can be exaggerated relative to other elements for clarity. Further, where considered appropriate, reference numerals can be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units can be at least partially implemented by a computer processor.

Generally, a system for soothing a baby during imaging by an imaging device is provided. The imaging device can be any device that requires the baby be still (or substantially still) during the imaging. For example, the imaging device can be a magnetic resonance imaging (MRI) device. In various embodiments, the imaging device is a positron emission tomography (PET) device, a computed tomography (CT) device and/or a PET/CT device.

The system can include a capsule incubator for positioning the baby within the imaging device. The capsule incubator can include a bottom portion having an inner surface, a bed positioned on top of the inner surface for positioning the baby thereon, and one or more members coupled to the bottom portion that are positioned in a first position to open the capsule incubator and a second position to close the capsule incubator.

The system can include a vibrational device. The vibrational device can include a vibrational element that extends from outside of the capsule incubator into the capsule incubator and is coupled to the bed to cause the bed to vibrate with a predetermined vibrational frequency, thus causing the baby to vibrate with the predetermined vibrational frequency. In some embodiments, the vibrational frequency is variable and is predetermined based on a frequency that a particular baby finds soothing and likely to cause the particular baby to sleep.

The description below (e.g., made with respect to FIGS. 1A, 1B and 1C, FIGS. 2A, 2B and 2C, FIGS. 3A, 3B and 3C and FIGS. 4A and 4B) provides an MRI device as an example for the imaging device. However, it would be apparent to those skilled in the art that some embodiments of the disclosed systems may be used with other imaging devices as well (e.g., PET/CT device).

Figure 1B:
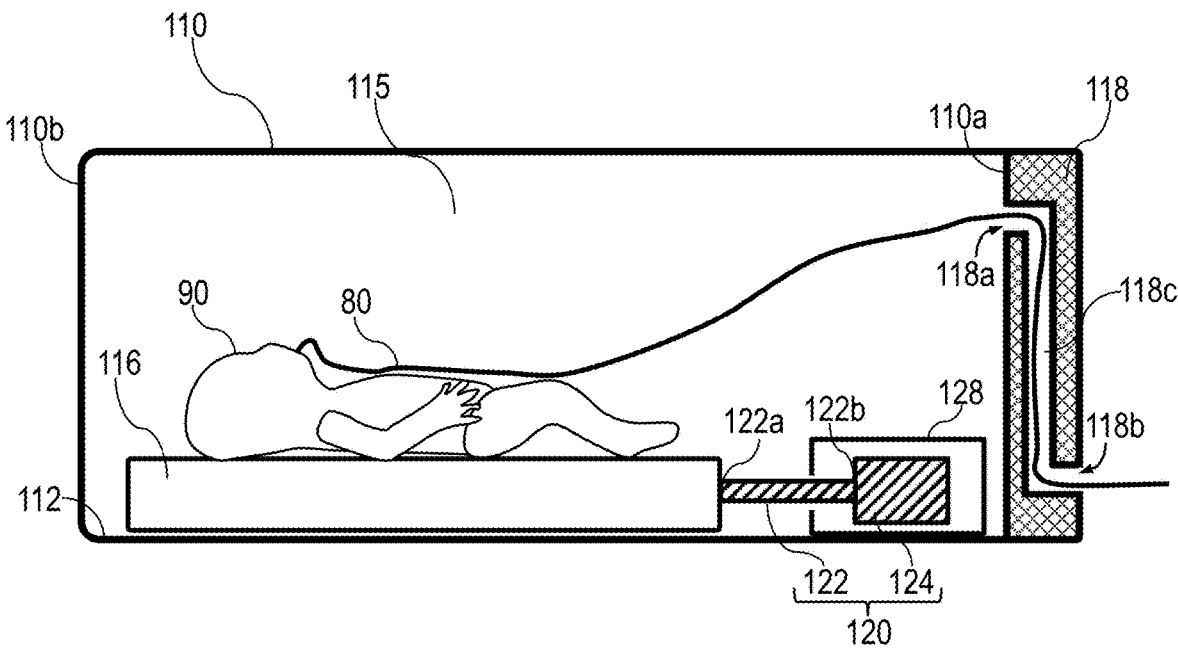
Figure 1C:
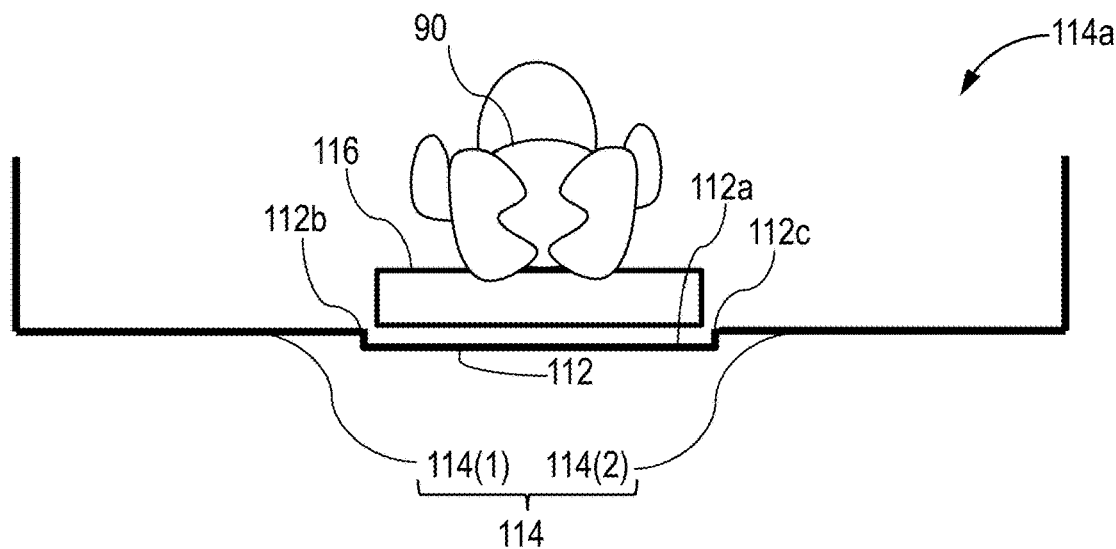
FIGS. 1C and 1D are schematic illustrations of a capsule incubator for a system for soothing a baby, according to some embodiments of the invention.
Figure 1D:
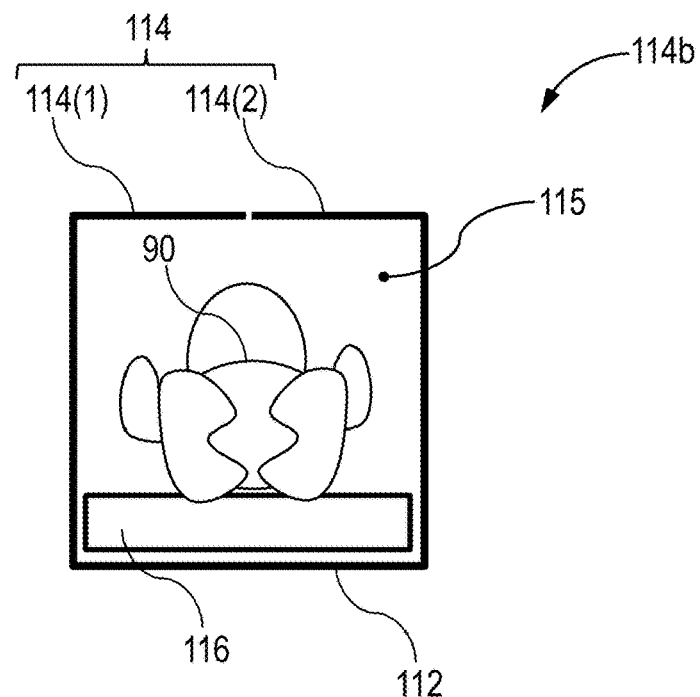

Reference is now made to FIGS. 1A and 1B, which are schematic illustrations of a system 100 for soothing a baby 90 during imaging, according to some embodiments of the invention. Reference is also made to FIGS. 1C and 1D, which are schematic illustrations of a capsule incubator 110 for a system for soothing a baby (such as system 100), according to some embodiments of the invention.

According to some embodiments, system 100 includes a capsule incubator 110 and a vibrational device 120 (e.g., as shown in FIGS. 1A and 1B).

According to some embodiments, capsule incubator 110 is adapted to receive and accommodate a baby 90. Baby 90 can be, for example, a human neonate. Capsule incubator 110 can be used to position baby 90 within an imaging device, such as, for example, a magnetic resonance imaging (MRI) device (e.g., as described below with respect to FIGS. 3A, 3B and 3C and FIGS. 4A and 4B).

Capsule incubator 110 can have a first capsule incubator end 110a, a second capsule incubator end 110b and a bottom portion 112 (e.g., as shown in FIGS. 1A and 1B). Bottom portion 112 can have an inner bottom portion surface 112a (e.g., as shown in FIGS. 1C and 1D).

In some embodiments, capsule incubator 110 includes one or more members 114 coupled to bottom portion 112 (e.g., as shown in FIGS. 1C and 1D). For example, capsule incubator 110 can include a first member 114(1) and a second member 114(2) rotatably coupled to opposite longitudinal edges 112b, 112c of bottom portion 112 with respect to each other (e.g., as shown in FIGS. 1C and 1D).

Member(s) 114 can be switchable between a first member position 114a (e.g., as shown in FIG. 1C) and a second member position 114b (e.g., as shown in FIG. 1D). When member(s) 114 is/are in first members position 114a, baby 90 can be inserted into capsule incubator 110 and positioned to rest on a bad 116 (e.g., as shown in FIG. 1C). Upon switching member(s) 114 into second member position 114b, member(s) 114 and bottom portion 112 can form a closed (or substantially closed) incubator interior 115 for baby 90 (e.g., as shown in FIGS. 1A, 1B and 1D).

In some embodiments, capsule incubator 110 is a transparent material. In some embodiments, capsule incubator 110 is a non-magnetic material. The transparent material can, for example, include poly-methyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, and/or polyvinyl chloride. In some embodiments, at least a portion of the transparent material is imbedded with non-transparent materials for means of strength and/or conductivity such as metallic wire.

In some embodiments, capsule incubator 110 includes a bed 116. Bed 116 can be movably positioned within capsule incubator 110 on inner bottom surface 112a thereof. The movable positioning thereof can enable vibration of bed 116 (and of baby 90) by vibrational device 120 (e.g., as described below with respect to FIGS. 2A, 2B and 2C).

In some embodiments, capsule incubator 110 includes a RF shield 118. RF shield 118 can detachably mate with, for example, first capsule incubator end 110a (e.g., as shown in FIGS. 1A and 1B).

RF shield 118 can have a first RF shield aperture 118a, a second RF shield aperture 118b and a conduit 118c extending through RF shield 118 between first RF shield aperture 118a and second RF shield aperture 118b (e.g., as shown in FIGS. 1A and 1B).

RF shield 118 can eliminate (or substantially eliminate) RF waves from exiting/entering capsule incubator 110 despite RF shield apertures 118a, 118b.

RF shield 118 can allow for one or more tubes 80 (e.g., present in capsule incubator 110 and/or attached to baby 90) to enter/exit capsule incubator 110 through conduit 118c, for example, without removing tube(s) 80 from baby 90 and without leakage of RF radiation into and/or out of capsule incubator 110. Tube(s) 80 can, for example, be medical tubes, life support tubes, monitors and/or any tubing that can need to be present within capsule incubator 110 and/or attached to baby 90.

In some embodiments, first RF shield aperture 118a coincides (or substantially coincides) with second RF shield aperture 118b (e.g., as shown in FIG. 1A). Accordingly, straight (or substantially straight) conduit 118c is formed.

In some embodiments, first RF shield aperture 118a is shifted with respect to second RF shield aperture 118b by a predetermined lateral shift (e.g., as shown in FIG. 1B). Accordingly, curved conduit 118c is formed.

A length to width ratio of conduit 118c can be determined to prevent leakage of RF radiation through conduit 118c into and/or out of capsule incubator 110. In some embodiments, conduit 118c has a length to width ratio of at least 5:1.

According to some embodiments, vibrational device 120 includes a vibrational element 122 and a vibrations generator 122 (e.g., as shown in FIGS. 1A and 1B). Vibrational element 122 can touch or can be coupled/connected (or detachably coupled/connected) to bed 116 at a first vibrational element end 122a and to vibrators generator 124 at a second vibrational element end 122b. Vibrational device 120 can cause bed 116 to vibrate with a predetermined vibrational frequency, thus causing baby 90 to vibrate with the predetermined vibrational frequency. Various embodiments of vibrational device 120 are described below with respect to FIGS. 2A, 2B and 2C.

Vibrations generator 124 can have the vibrational frequency that varies. The vibration frequency can be based on preference of baby 90. For example, a vibration frequency that soothes one baby cannot soothe another baby. Thus, allowing the vibration frequency to vary can allow babies having different soothing rates to each be soothed by vibrational device 120. Vibrating baby 90 can, for example, cause the baby to fall asleep and thus remain still (or substantially still) during imaging.

In some embodiments, vibrations generator 124 is positioned external to capsule incubator 110 (e.g., as shown in FIG. 1A). In these embodiments, vibrational element 122 extends from capsule incubator 110 outside/external to capsule incubator 110 through conduit 118c.

In some embodiments, vibrational device 120 is positioned within capsule incubator 110 (e.g., as shown in FIG. 1B). In these embodiments, at least a portion of vibrational device 120 (e.g., vibrations generator 124 and at least a portion of vibrational element 122) is positioned within an RF shield structure 128 (e.g., as shown in FIG. 1B). RF shield structure 128 can be, for example, a Faraday's cage.

Figure 2A:
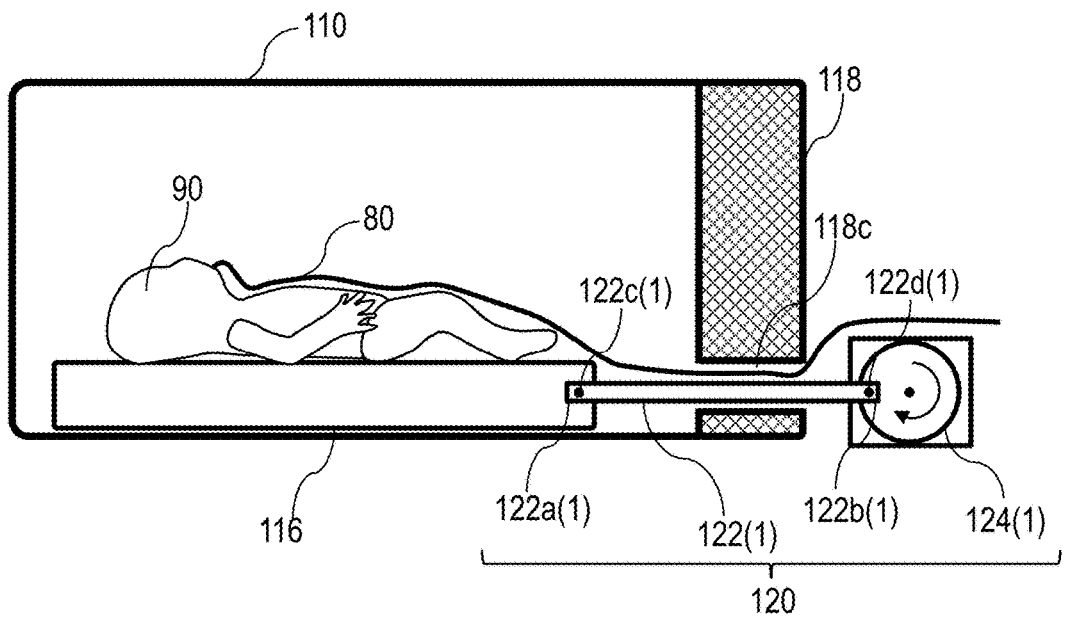
FIGS. 2A, 2B and 2C are schematic illustrations of various configurations of a vibrational device for a system for soothing a baby during imaging, according to some embodiments of the invention.
Figure 2B:
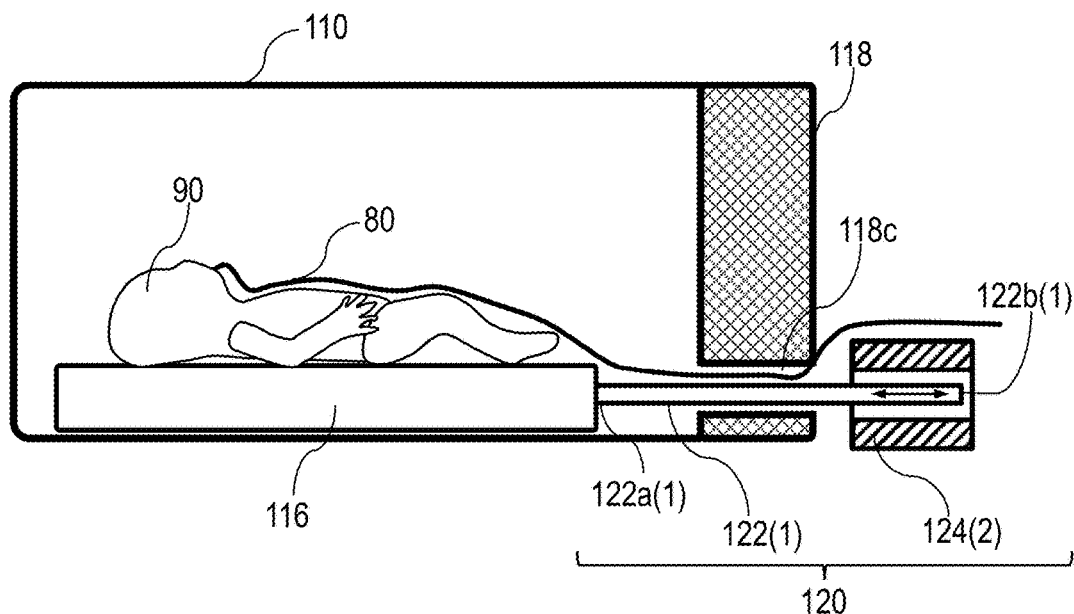
Figure 2C:
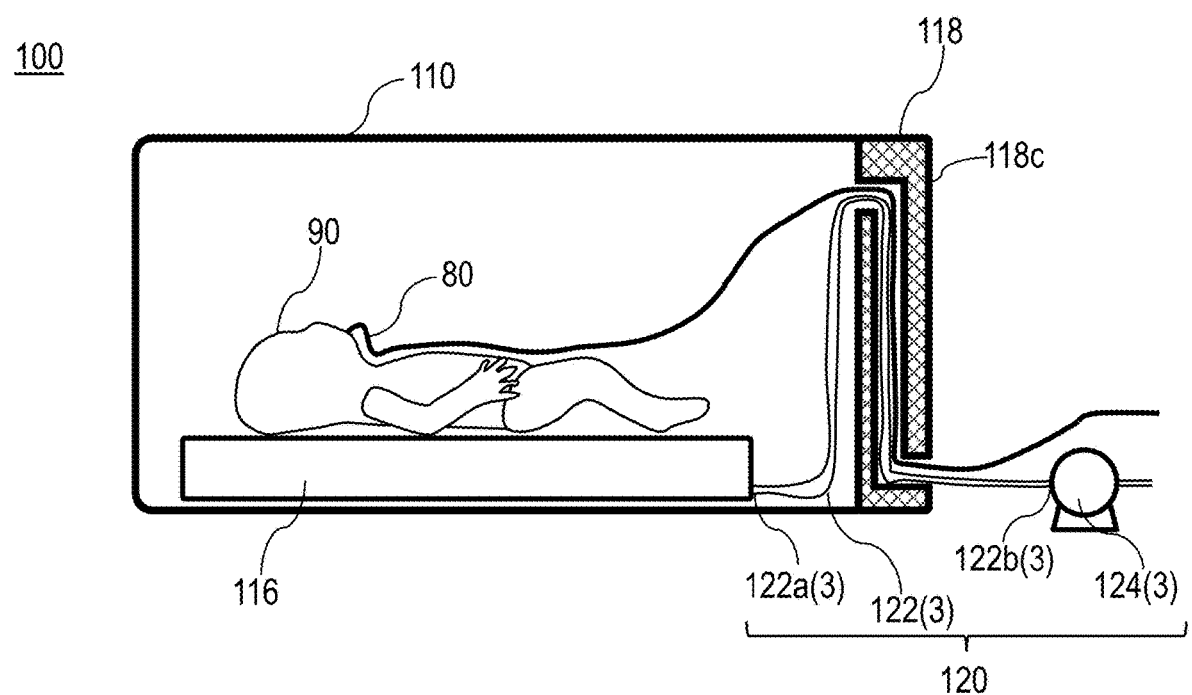

Reference is now made to FIGS. 2A, 2B and 2C, which are schematic illustrations of various configurations of a vibrational device 120 for a system for soothing a baby 90 during imaging (such as system 100), according to some embodiments of the invention.

According to some embodiments, vibrational device 120 includes a rod 122(1) and a rotating device 124(1) (e.g., vibrational element 122 and vibrational generator 124, respectively, as described above with respect to FIGS. 1A and 1B) (e.g., as shown in FIG. 2A). In some embodiments, the rod 122(1) is made of a non-magnetic material.

Rod 122(1) can have a first rod end 122a(1) and a second rod end 122b(1). Rod 122(1) can be pivotally coupled to bed 116 at, for example, first rod end 122a(1) and/or can be pivotally coupled to rotating device 124(1) at, for example, second rod end 122b(1) (e.g., using pivots 122c(1) and 122d(1), respectively) (e.g., as shown in FIG. 2A).

Rod 122(1) can extend from capsule incubator 110 to an environment that is external to capsule incubator 110 through conduit 118c (e.g., as shown in FIG. 2A and as described above with respect to FIGS. 1A and 1B). The rod 122(1) can be positioned to be directly coupled to the bed 116 to cause the bed 116 to vibrate (e.g., rod 122(1) can be positioned under the bed 116, on the side of the bed 116, and/or positioned within a slot in the bed 116). In some embodiments, a overlay can be positioned on top of the bed 116 and the rod 122(1) can be positioned between the overlap and the bed 116, such that the rod 122(1) vibrates the overlay and a baby can lie on the overlay. The overlay can be a mattress pad.

According to some embodiments, vibrational device 120 includes rod 122(1) and an electric vibrator device 124(2) (e.g., vibrational element 122 and vibrational generator 124, respectively, as described above with respect to FIGS. 1A and 1B) (e.g., as shown in FIG. 2B). In some embodiments, the vibrational device 120 is an eccentric rotation plate and/or mass device.

It is noted that using of vibrational device 120 having rod 122(1) can, in some embodiments, require straight (or substantially straight) conduit 118c (e.g., as shown in FIGS. 2A and 2B and as described above with respect to FIG. 1A)

According to some embodiments, vibrational device 120 includes a fluid conduit 122(3) and a fluid pump 124(3) (e.g., vibrational element 122 and vibrations generator 124, respectively, as described above with respect to FIGS. 1A and 1B) (e.g., as shown in FIG. 2C). In some embodiments, fluid conduit 122(3) is made of a non-magnetic material.

Fluid conduit 122(3) can have a first fluid conduit end 122a(3) and a second fluid conduit end 122b(3). Fluid conduit 122(3) can be coupled to/touch bed 116 at, for example, first fluid conduit end 122a(3) and can be coupled to fluid pump 124(3) at second fluid conduit end 122b(3) (e.g., as shown in FIG. 2C). Fluid pump 124(3) can pump fluid into fluid conduit 122(3) in a manner that causes a vibration of bed 116, and thus baby 90 positioned thereon. In some embodiments, the conduit 122(3) is positioned below the bed.

For example, fluid conduit 122(3) can be made of a flexible material and fluid pump 124(3) can generate a pulsatile flow into fluid conduit 122(3). Thus fluid conduit 122(3) can expand and/or collapse in response to the pulsatile flow, thereby vibrating bed 116 and baby 90 positioned thereon.

It is noted that fluid conduit 122(3) can be used with RF shield 130 having any of straight conduit 118c (not shown in FIG. 2C) or curved conduit 118c (e.g., as shown in FIG. 2C).

Figure 3A:
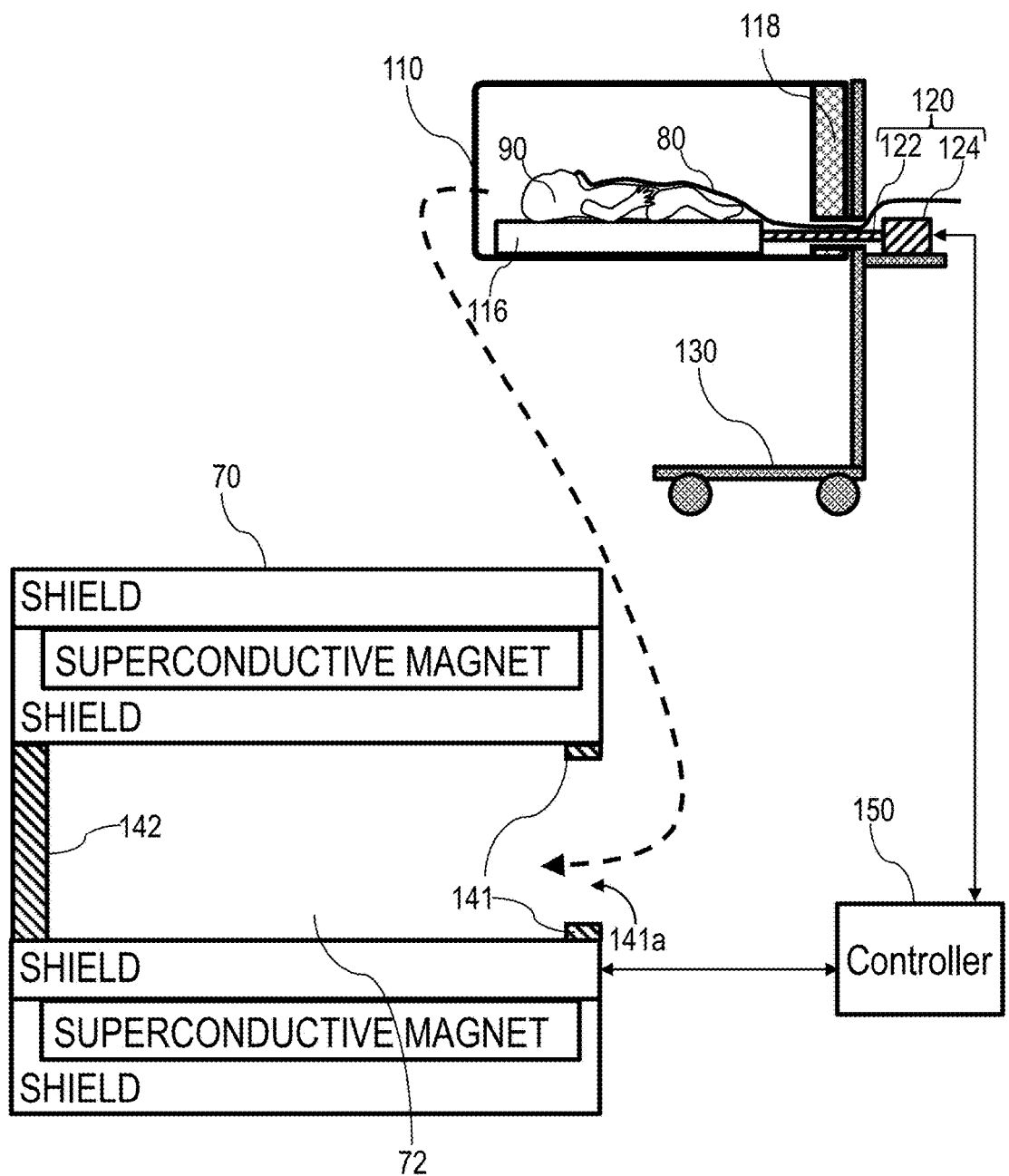
FIGS. 3A, 3B and 3C are schematic illustrations of a system for soothing a baby in operation with an imaging device, according to some embodiments of the invention.
Figure 3B:
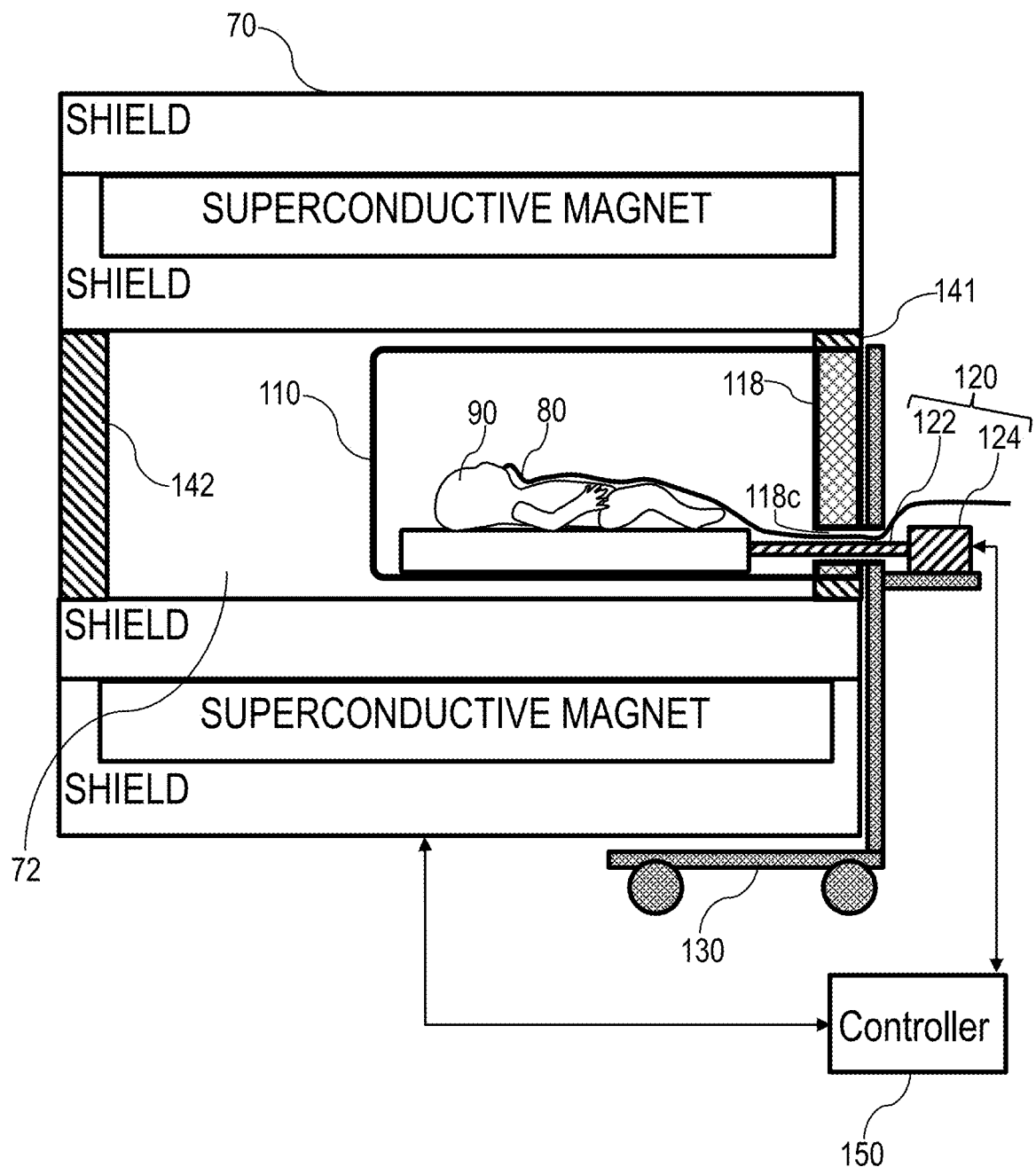
Figure 3C:
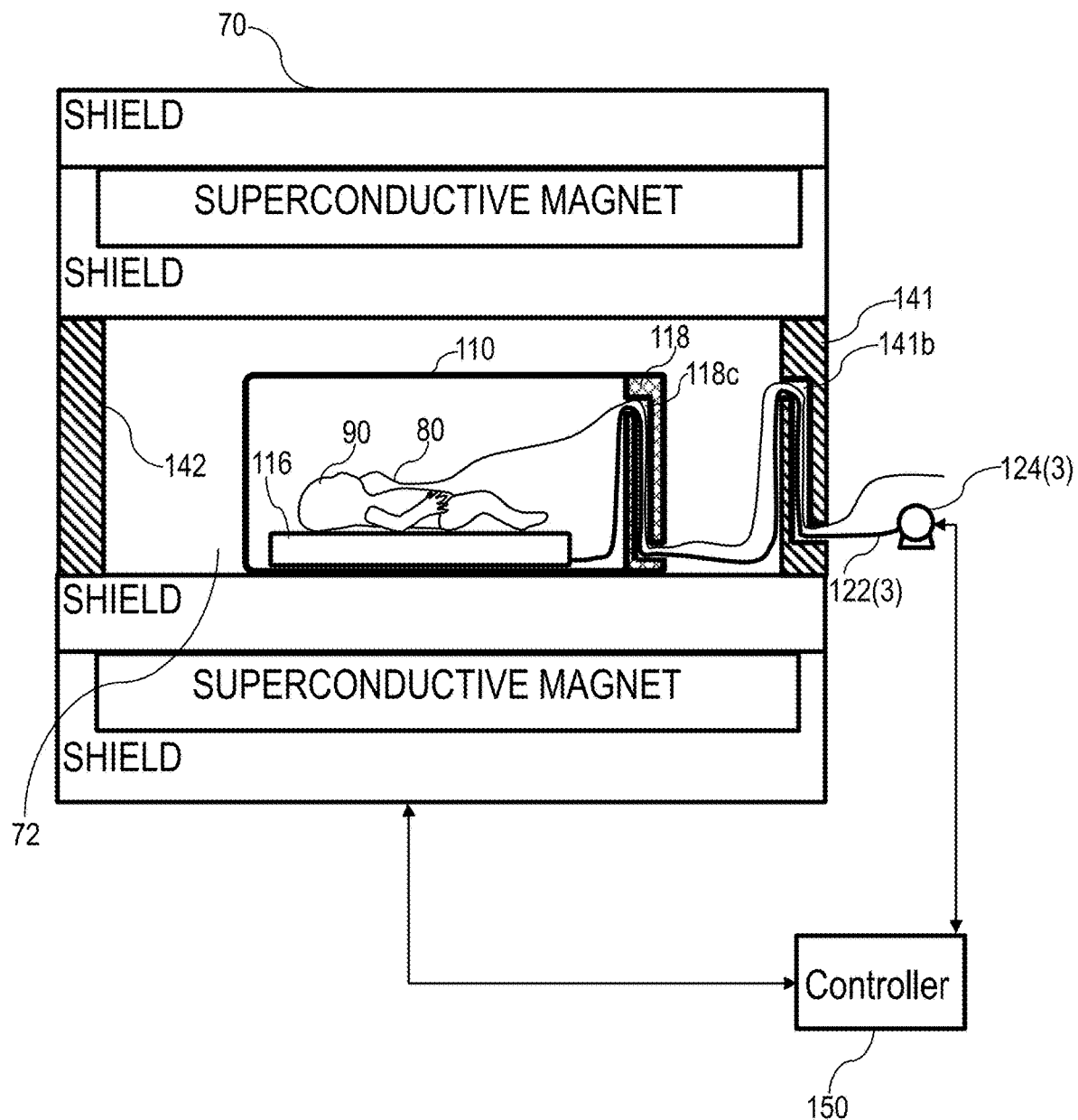

Reference is now made to FIGS. 3A, 3B and 3C, which are schematic illustrations of a system 100 for soothing a baby 90 in operation with an imaging device 70, according to some embodiments of the invention.

According to some embodiments, system 100 includes a cart 130 (e.g., as shown in FIGS. 3A and 3B). Cart 130 can be detachably couplable to capsule incubator 110 (e.g., at first incubator end 110a). Cart 130 can be used to transport capsule incubator 110 and/or vibrational device 120 to a desired location. For example, cart 130 can be used to transport capsule incubator 110 and/or position capsule incubator 110 within an imaging device 70.

Imaging device 70 can, for example, be a magnetic resonance imaging (MRI) device. In some embodiments, MRI device 70 is a superconductor MRI device known in the art (e.g., as shown in FIGS. 3A, 3B and 3C).

Capsule incubator 110 can be transported, e.g. using cart 130, and positioned within a bore 72 of MRI device 70 to image baby 90 (e.g., as indicated by a dashed arrow in FIG. 3A).

In some embodiments, superconductor magnet MRI device 70 includes a first RF and magnetic shielding door 141 and a second RF and magnetic shielding door 142 (e.g., as shown in FIGS. 3A, 3B and 3C). RF and magnetic shielding doors 141 and 142 can be made of a material that substantially shields RF and magnetic fields. Doors 141 and 142 can be retrofit onto existing superconductor magnet MRI devices. In this manner, superconductor magnet MRI devices can be removed from MRI shielded rooms and put in any location for, for example, imaging baby 90 within the capsule incubator 110.

In some embodiments, door 141 includes an opening 141a (e.g., as shown in FIG. 3A) that allows RF shield 118 coupled to capsule incubator 110 to seal opening 141a of door 141 (e.g., as shown in FIG. 3B) such that the RF and magnetic radiation does not enter/exit bore 72 of superconductor magnet MRI device 70.

In some embodiments, capsule incubator 110 does not detach from cart 130 while the medical procedure (e.g., imaging) occurs (e.g., as shown in FIG. 3B).

In some embodiments, vibrations generator 124 of vibrational device 120 is positioned external to bore 72 of MRI device 70. For example, vibrational device 120 can be positioned on/coupled to cart 130 (e.g., as shown in FIG. 3B). Vibrational element 122 can be introduced through conduit 118c into incubator interior 115 of capsule incubator 110 positioned within bore 72 of MRI device 70 (e.g., as shown in FIG. 3B).

In some embodiments, capsule incubator 110 is detached from cart 130 while the imaging occurs. In these embodiments, the entire capsule incubator 110 is positioned within bore 72 of MRI device 70 (e.g., as shown in FIG. 3C). Door 141 can include a door RF shielding conduit 141b having a length to width ratio (e.g., 5:1). Door RF shielding conduit 141b can enable introduction of tube(s) 80 and/or of vibrational element 122 into bore 72 of MRI device 70 while eliminating (or substantially eliminating) RF waves from exiting/entering bore 72 of MRI device 70.

In these embodiments, fluid pump 124(3) and fluid conduit 122(3) can be used as vibrations generator 124 and vibrational element 122, respectively (e.g., as described above with respect to FIG. 2C) to, for example, enable easy introduction of vibrational element 122 into bore 72 of MRI device 70 (e.g., as shown in FIG. 3C). It would be apparent to those skilled in the art, that other embodiments of vibrational device 120 (e.g., those described above with respect to FIGS. 2A and 2B) can be used as well.

In this manner (e.g., as described above with respect to FIGS. 3A, 3B and 3C), vibrations can be provided to baby 90 without causing a leakage of RF radiation from/into MRI device 70.

Vibrating baby 90 can cause the baby to move, and thus can add unwanted motion artifacts in the MRI images generated by MRI device 70. Since the vibrational frequency of vibrations generator 124 and of baby 90 is known, the movement of baby 90 can be accounted for, and the effects of the vibration/movement can be accounted for during, for example, the imaging and/or during the post processing of the MRI images.

According to some embodiments, system 100 includes a controller 150. Controller 150 can be in communication (e.g., wired or wireless) to vibrational device 120 (e.g., to vibrations generator 124) and/or to MRI device 70.

Controller 150 can control the operation of vibrational device 120 and/or the operation of MRI device 70 during imaging of baby 90 to, for example, account for the effects of the vibration/movement of baby 90 during the imaging.

In some embodiments, controller 150 stops the vibrations generated by vibrations generator 124 each time MRI device 70 scans. In some embodiments, controller 150 synchronizes MRI device 70 to perform scans at the same relative location in the vibration cycle of vibrations generator 124.

According to some embodiments, MRI images generated by MRI device 70 can be filtered (e.g., during post-processing) to correct for a phase effect generated by scanning different k-space locations at different times during the vibration cycle of vibrations generator 124. The filtering can, for example, remove or correct a portion of the MRI images at the vibrational frequency.

Figure 4A:
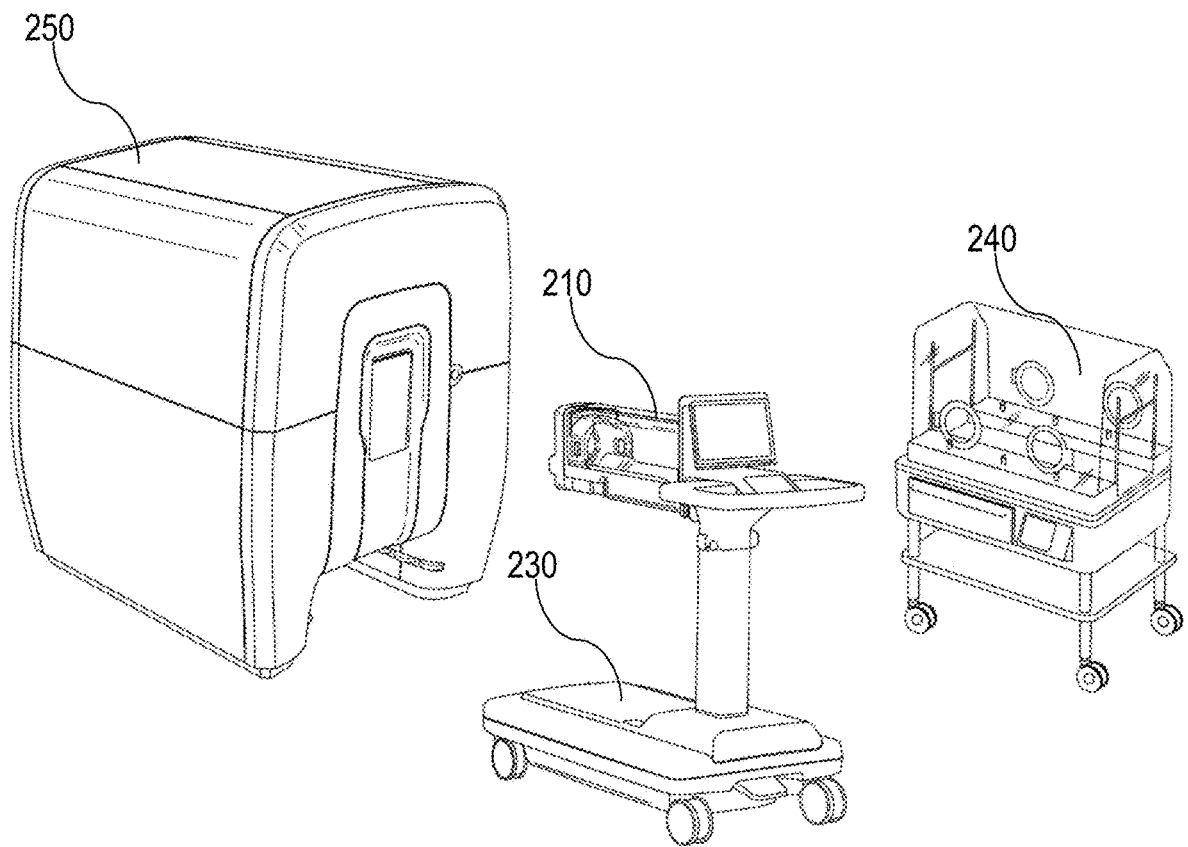
FIGS. 4A and 4B are schematic illustrations of a system for housing, transporting and imaging a baby, according to some embodiments of the invention.
Figure 4B:
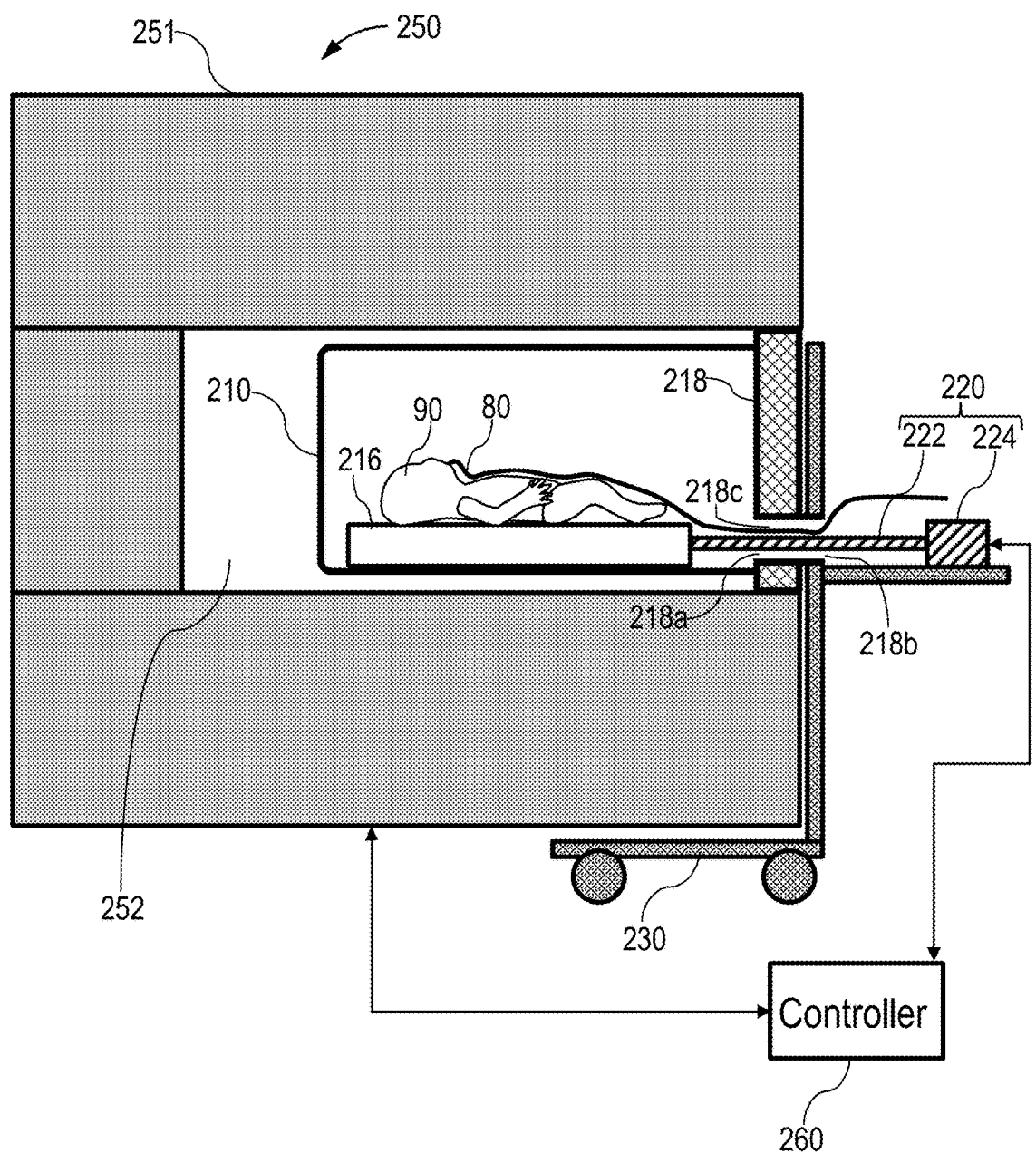

Reference is now made to FIGS. 4A and 4B, which are schematic illustrations of a system 200 for housing, transporting and imaging a baby 90, according to some embodiments of the invention.

According to some embodiments, system 200 includes a capsule incubator 210, a vibrational device 220, a cart 230, a dock incubator 240, an imaging device 250 and a controller 260. It is noted that vibrational device 220 and controller 260 are not shown in FIG. 4A and that dock incubator 240 is not shown in FIG. 4B for sake of clarity only.

In some embodiments, capsule incubator 210 is similar to capsule incubator 110 described above with respect to FIGS. 1A, 1B and 1C. In some embodiments, vibrational device 220 is similar to vibrational device 120 described above with respect to FIGS. 2A, 2B and 2C. In various embodiments, cart 230 and/or controller 260 are similar to cart 130 and controller 150, respectively, described above with respect to FIGS. 3A, 3B and 3C.

During operation, baby 90 (not shown in FIG. 4A) lies on a bed 216 within capsule incubator 210. Capsule incubator 210 can be positioned within dock incubator 240, connected to cart 230, or positioned within MRI device 250. In some embodiments, capsule incubator 210 is positioned in any desired location (e.g., other imaging devices, examination table and/or operating table).

Capsule incubator 210 can be moved between dock incubator 240 and MRI device 250 (or any desired location) via cart 230. Life support equipment 80 (not shown in FIG. 4A) attached to baby 90 can remain intact when moving baby 90 from dock incubator 240 to a desired location via cart 230 and capsule incubator 210. The environment (e.g., temperature, humidity, noise level, vibration level, light level and/or bacteria/germ) surrounding baby 90 in dock incubator 240 can be maintained in capsule incubator 210 during movement of the baby in capsule incubator 210.

In some embodiments, baby 90 is moved from dock incubator 240 in capsule incubator 210 attached to cart 230, to a desired location, and capsule incubator 210 does not detach from cart 230 while the medical procedure occurs (e.g., imaging using the MRI device 250 with a bore to receive the capsule incubator 210). Baby 90 can be moved from dock incubator 240 to the medical procedure and back to dock incubator 240 via the capsule incubator 210 and cart 230 without ever moving the life support equipment 80 of baby 90 from cart 210 or the modifying the environment of baby 90.

In some embodiments, baby 90 is moved from dock incubator 240 in capsule incubator 210 attached to cart 230, to a desired location, and capsule incubator 210 detaches from cart 230. Baby 90 can be moved from dock incubator 240 to the desired location via capsule incubator 210 without removing the life support equipment from the baby.

MRI device 250 can include a housing 251 (e.g., as shown in FIG. 4B). Housing 251 can be made of a material that shields an environment exterior to MRI device 250 from the magnetic fields generated by magnets (e.g., magnetic fringe fields), such as permanent magnets, within MRI device 250 and RF energy generated by one or more RF coils within MRI device 250 or inserted into MRI device 250 (not shown). Housing 251 of MRI device 250 can also prevent magnetic fields and RF energy exterior to MRI device 250 from entering MRI device 250, and thus causing interference in the imaging results. MRI device 250 can be a permanent magnet-based MRI. MRI device 250 can be an MRI device as described in U.S. Pat. No. 7,400,147 and/or U.S. Pat. No. 7,315,168, both of which are incorporate herein by reference in their entireties.

Capsule incubator 210 can include a RF shield 218 at, for example a first incubator end 210a that, for example, mates with cart 230 (e.g., as shown in FIG. 4B). RF shield 218 can include at least two RF shield apertures 218a, 218b and an conduit 218c extending between RF shield apertures 218a, 218b (e.g., as shown in FIG. 4B). RF shield 218 can eliminate (or substantially eliminate) RF waves from entering/exiting capsule incubator 210 despite apertures 218a, 218b. For example, RF shield 218, RF shield apertures 218a, 218b and/or conduit 218c can be similar to RF shield 118, RF shield apertures 118a, 118b and conduit 118c described above with respect to FIGS. 1A, 1B and 1C.

In some embodiments, RF shield 218 mates with a bore 252 of MRI device 250. In some embodiments, when capsule incubator 210 is positioned within bore 252 of MRI device 250, the walls of bore 252 enclose conduit 218 to form a conduit that is completely (or substantially completely) closed.

When capsule incubator 210 is inserted into MRI device 250, RF shielding 218 mates with and closes (or substantially closes) bore 252 of MRI device 250 (e.g., as shown in FIG. 4B). A vibrational element 222 of vibrational device 220 coupled to bed 216 within capsule incubator 210 can extend from an interior of bore 252 of MRI device 250 through RF shielding conduit 218c, external to MRI device 250, where vibrational element 222 can be coupled to a vibrations generator 224 of vibrational device 220. For example, vibrational element 222 and/or vibrations generator 224 can be similar to vibrational elements 122 and vibrations generators 124, respectively, described above with respect to FIGS. 2A, 2B, 2C.

In this manner, vibrations can be provided to baby 90 without causing a leakage of RF radiation from/into MRI device 250.

Controller 260 can be in communication (e.g., wired or wireless) to vibrational device 220 (e.g., to vibrations generator 224) and/or to MRI device 250. Controller 260 can control the operation of vibrational device 220 and/or the operation of MRI device 250 during imaging of baby 90 to, for example, account for the effects of the vibration/movement of baby 90 during the imaging (e.g., as described above with respect to FIGS. 3A, 3B and 3C).

Figure 5:
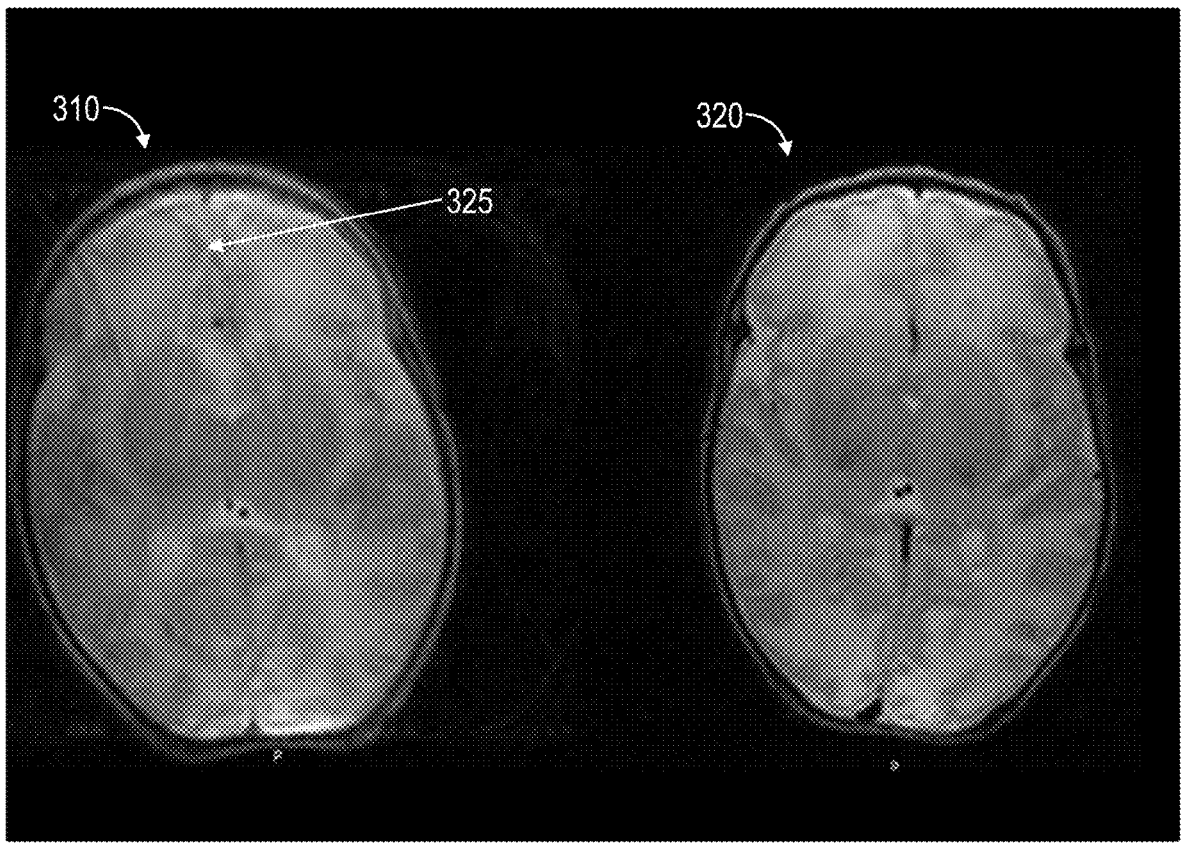
FIG. 5 which are examples of a head magnetic resonance (MRI) image of a baby that is moving and an MRI image of the same baby that is not moving during imaging, respectively.

Reference is now made to FIG. 5, which are examples of a head magnetic resonance (MRI) image of a baby that is moving and an MRI image of the same baby that is not moving during imaging, respectively.

An MRI image 310 is the MRI image of the baby awake during imaging. An MRI image 320 is the MRI image of the baby that is sleeping (and thus not moving) during imaging. As can be seen in MRI image 310, when the baby is moving unwanted bright spots (e.g., bright stripes 325) and/or extraneous lines can be generated that are not actually there (compare against same location in 320). This can cause misdiagnosis, possibility for additional unnecessary testing, and overall uncertainty of the MRI image.

The description above (e.g., made with respect to FIGS. 1A, 1B and 1C, FIGS. 2A, 2B and 2C, FIGS. 3A, 3B and 3C and FIGS. 4A and 4B) provides the MRI device as an example of the imaging device. However, it would be apparent to those skilled that some embodiments of the disclosed systems may be used with other imaging devices as well. It would be also apparent to those skilled in the art that while the MRI device can require usage of RF and/or magnetic shielding within the systems disclosed above (e.g., RF shields 118, 218 and RF and magnetic shielding doors 141, 142 described above), these shields may not be required while using some other imaging devices.

Figure 6:
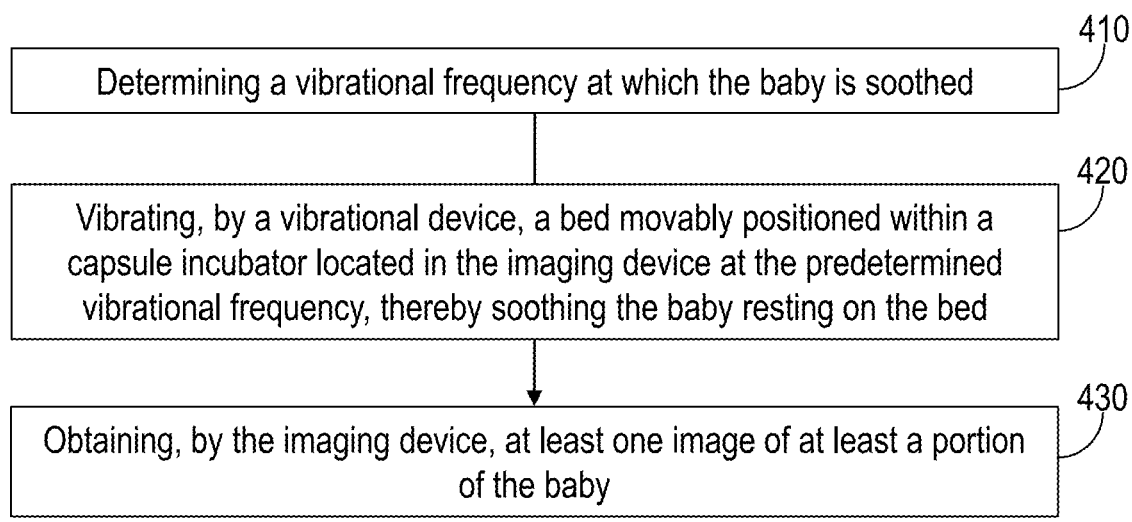
FIG. 6 is a flowchart of a method of soothing a baby during imaging by an imaging device, according to some embodiments of the invention.

Reference is now made to FIG. 6, which is a flowchart of a method 400 of soothing a baby during imaging by an imaging device, according to some embodiments of the invention.

Method 400 can be implemented by a system for soothing a baby (such as system 100 and/or system 200 described above), which can be configured to implement method 400. It is noted that method 400 is not limited to the flowcharts illustrated in FIG. 6 and to the corresponding description. For example, in various embodiments, method 400 needs not move through each illustrated box or stage, or in exactly the same order as illustrated and described.

According to some embodiments, method 400 includes determining a vibrational frequency at which the baby is soothed (stage 410).

According to some embodiments, method 400 includes vibrating, by a vibrational device, a bed movably positioned within a capsule incubator located in the imaging device at the predetermined vibrational frequency, thereby soothing the baby resting on the bed (stage 420) (e.g., as described above with respect to FIGS. 1A, 1B and 1C and FIGS. 2A, 2B and 2C).

In some embodiments, method 400 includes providing a radiofrequency (RF) and/or magnetic shield to the vibrational device to prevent from RF and/or magnetic radiation generated by the MRI device to interfere with the vibrational device (e.g., as described above with respect to FIGS. 1A, 1B and 1C, FIGS. 2A, 2B and 2C, FIGS. 3A, 3B and 3C and FIGS. 4A and 4B).

According to some embodiments, method 400 includes obtaining, by the imaging device, at least one image of at least a portion of the baby (stage 430).

In some embodiments, method 400 further includes stopping the vibrations generated by the vibrational device each time the imaging device scans (e.g., as described above with respect to FIGS. 3A, 3B and 3C).

In some embodiments, method 400 further includes synchronizing the imaging device to perform scans at the same relative location in a vibrational cycle of the vibrational device (e.g., as described above with respect to FIGS. 3A, 3B and 3C).

In some embodiments, method 400 further includes filtering the at least one image to correct for a phase effect generated by scanning different spatial locations at different times during the vibrational cycle of the vibrational device (e.g., as described above with respect to FIGS. 3A, 3B and 3C).

Advantages of the present invention can include soothing a baby to sleep according to a preferred vibrational frequency of each particular baby during, for example, an MRI treatment such that the MRI is taken when the baby is motionless. Another advantage of the present invention can include an ability to obtain an MRI image of a baby without a dedicated MRI room. Another advantage of the technology can include the ability to obtain a MRI of a baby with a MRI device that substantially eliminates a magnetic fringe field outside of the device, such that, for example, a vibrator element, an electronic equipment, metal and other objects that typically need to be shielded from an MRI (e.g., via an MRI shield room) can be positioned anywhere nearby the MRI device.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A system for soothing a baby during imaging by an imaging device, the system comprising:
    a capsule incubator for positioning the baby within the imaging device, the capsule incubator comprising:
        a bottom portion having an inner surface,
        a bed positioned on top of the inner surface for positioning the baby thereon, and
        one or more members coupled to the bottom portion that are positioned in a first position to open the capsule incubator and a second position to close the capsule incubator; and
    a vibrational device comprising a vibrational element that extends from outside of the capsule incubator into the capsule incubator and is coupled to the bed to cause the bed to vibrate with a predetermined vibrational frequency, thus causing the baby to vibrate with the predetermined vibrational frequency.

2. The system of claim 1 operable with a magnetic resonance imaging (MRI) device, wherein:
    the capsule incubator further comprises a radio frequency (RF) shield that detachably mates with a first incubator end of the capsule incubator, the RF shield comprising a conduit having a first aperture and a second aperture; and
    wherein the vibrational element extends from the outside of the capsule incubator into the capsule incubator through the conduit.

3. The system of claim 2, wherein the conduit has a length to width ratio of at least 5 to 1.

4. The system of claim 1, wherein the vibrational device further comprises a vibrations generator positioned outside of the capsule incubator, and wherein the vibrational element is a rod coupled to the vibrations generator.

5. The system of claim 1, wherein the vibrational device further comprises a fluid pump positioned outside of the capsule incubator, and the vibrational element is a fluid conduit coupled to the fluid pump.

6. The system of claim 1, further comprising a cart detachably connectable to the first incubator end of the capsule incubator and capable of transporting the capsule incubator and of positioning the capsule incubator within the imaging device.

7. The system of claim 1, further comprising a controller in communication with the vibrational device and the imaging device, the controller to at least one of:
   stop the vibrations generated by the vibrational device each time the imaging device scans; and
   synchronize the imaging device to perform scans at the same relative location in the vibration cycle of vibrational device.

8. A system for housing, transporting and imaging a baby, the system comprising:
   a magnetic resonance imaging (MRI) device comprising:
      a magnetic field assembly comprising at least one magnet, at least one radiofrequency (RF) coil and a bore, the magnetic field assembly to generate a magnetic field to carry out the imaging of the baby, and
      a housing to at least partly surround the magnetic field assembly and to substantially eliminate a magnetic fringe field generated by the magnetic field assembly outside the housing;
   a capsule incubator for positioning the baby within the bore of the MRI device, the capsule incubator comprising:
      a bottom portion having an inner surface,
      a bed positioned on top of the inner surface for positioning the baby thereon,
      one or more members coupled to the bottom portion that are positioned in a first position to open the capsule incubator and a second position to close the capsule incubator, and
      radio frequency (RF) shield that detachably mates with a first incubator end of the capsule incubator and closes the bore of the MRI device when the capsule incubator is positioned therein, the RF shield comprising a conduit having a first aperture and a second aperture; and
   a vibrational device comprising:
      a vibrations generator positioned outside the capsule incubator and capable of generating vibrations at a predetermined vibrational frequency, and
      a non-magnetic vibrational element that extends from outside of the capsule incubator into the capsule incubator through the conduit and is coupled to the vibrations generator at a first element end and to the bed at a second element end to cause the bed to vibrate with the predetermined vibrational frequency, thus causing the baby to vibrate with the predetermined vibrational frequency,
      wherein the predetermined frequency is based on a frequency that a particular baby finds soothing and likely to cause the particular baby to sleep.

9. The system of claim 8, wherein the conduit has a length to width ratio of at least 5 to 1.

10. The system of claim 8, wherein the vibrations generator is a rotational or an electrical device.

11. The system of claim 8, wherein the vibrations generator is a fluid pump and the vibrational element is a non-magnetic fluid conduit.

12. The system of claim 8, further comprising a cart detachably connectable to the first incubator end of the capsule incubator and capable of transporting the capsule incubator and of positioning the capsule incubator within the imaging device.

13. The system of claim 8, further comprising a controller in communication with the vibrational device and the MRI device, the controller to at least one of:
   stop the vibrations generated by vibrational device each time the MRI device scans; and
   synchronize the MRI device to perform scans at the same relative location in the vibration cycle of vibrational device.

14. A method of soothing a baby during imaging by an imaging device, the method comprising:
   determining a vibrational frequency at which the baby is soothed;
   vibrating, by a vibrational device, a bed movably positioned within a capsule incubator located in the imaging device at the predetermined vibrational frequency, thereby soothing the baby resting on the bed; and
   obtaining, by the imaging device, at least one image of at least a portion of the baby.

15. The method of claim 14, further comprising providing a radiofrequency (RF) and/or magnetic shield to the vibrational device to prevent from RF and/or magnetic radiation generated by the MRI device to interfere with the vibrational device.

16. The method of claim 14, further comprising at least one of:
   stopping the vibrations generated by the vibrational device each time the imaging device scans;
   synchronizing the imaging device to perform scans at the same relative location in a vibrational cycle of the vibrational device; and
   filtering the at least one image to correct for a phase effect generated by scanning different spatial locations at different times during the vibrational cycle of the vibrational device.

* * * * *